United States Patent
Kawamata et al.

(10) Patent No.: US 12,408,895 B2
(45) Date of Patent: Sep. 9, 2025

(54) ULTRASOUND PROBE AND ULTRASOUND DIAGNOSTIC APPARATUS

(71) Applicant: FUJIFILM Healthcare Corporation, Kashiwa (JP)

(72) Inventors: Tsuneo Kawamata, Chiba (JP); Kengo Imagawa, Chiba (JP); Takayuki Iwashita, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 18/504,677

(22) Filed: Nov. 8, 2023

(65) Prior Publication Data

US 2024/0156435 A1    May 16, 2024

(30) Foreign Application Priority Data

Nov. 10, 2022  (JP) ................................. 2022-180142
Oct. 6, 2023   (JP) ................................. 2023-174159

(51) Int. Cl.
*A61B 8/00* (2006.01)
*G01S 15/89* (2006.01)

(52) U.S. Cl.
CPC ........ *A61B 8/4488* (2013.01); *G01S 15/8925* (2013.01)

(58) Field of Classification Search
CPC ....... A61B 8/4488; A61B 8/4494; A61B 8/54; G01S 15/8925; G01S 15/8915; G01S 15/8927

See application file for complete search history.

(56) References Cited

U.S. PATENT DOCUMENTS

| 2015/0297183 | A1* | 10/2015 | Freeman | A61B 8/4444 600/459 |
| 2017/0285150 | A1* | 10/2017 | Chen | G01S 7/5205 |
| 2021/0282749 | A1* | 9/2021 | Notten | A61B 8/4444 |

FOREIGN PATENT DOCUMENTS

| JP | H1170111 | * 3/1999 |
| JP | 2012-152317 A | 8/2012 |

OTHER PUBLICATIONS

JP H1170111 machine translation (Year: 1999).*

* cited by examiner

*Primary Examiner* — Alexei Bykhovski
(74) *Attorney, Agent, or Firm* — Paul Teng

(57) ABSTRACT

The number of signal lines connecting an ultrasound probe and an apparatus main body of an ultrasound diagnostic apparatus can be reduced while suppressing reduction of the maximum opening width of the ultrasound probe. A transducer array is conceptually divided into a plurality of center-side main transducers located on a center side of an arrangement, a plurality of first end-side main transducers located on a first end side of the arrangement with respect to the plurality of center-side main transducers, and a plurality of second end-side main transducers located on a second end side with respect to the plurality of center-side main transducers. A connection circuit is configured to include a first circuit connecting a transmission and reception circuit and the center-side main transducer, and a second circuit provided with a switch as a main transducer switching switch for switching a connection destination of the transmission and reception circuit between the first end-side main transducer and the second end-side main transducer.

7 Claims, 9 Drawing Sheets

ULTRASOUND PROBE AND ULTRASOUND DIAGNOSTIC APPARATUS

CROSS-REFERENCE TO RELATED APPLICATIONS

The present application claims priority from Japanese Patent Applications Nos. 2022-180142 and 2023-174159 filed on Nov. 10, 2022 and Oct. 6, 2023, respectively, the content of each of which is hereby incorporated by reference into this application.

BACKGROUND OF THE INVENTION

1. Field of the Invention

The present specification discloses improvement of an ultrasound probe and improvement of an ultrasound diagnostic apparatus.

2. Description of the Related Art

In the related art, there has been known an ultrasound diagnostic apparatus that transmits and receives an ultrasonic wave to and from a subject, forms an ultrasound image based on a reception signal obtained by the transmission and reception of the ultrasonic wave, and displays the formed ultrasound image. In general, the ultrasound diagnostic apparatus is configured to include an ultrasound probe, an apparatus main body, and a monitor. The ultrasound probe transmits and receives an ultrasonic wave to and from a subject. The apparatus main body performs a process of transmitting a transmission signal for causing the ultrasound probe to transmit the ultrasonic wave, a process of forming an ultrasound image based on a reception signal from the ultrasound probe, or the like. The monitor displays the ultrasound image formed by the apparatus main body.

In recent years, a wireless probe has also been proposed, but there are still many cases where the apparatus main body and the ultrasound probe are connected via a cable. The ultrasound probe has a transducer array including a large number of transducers (for example, hundreds of transducers) for transmitting and receiving the ultrasonic wave. Therefore, in order for the apparatus main body to send the transmission signal to each transducer or for the apparatus main body to receive the reception signal from each transducer, the cable connecting the apparatus main body and the ultrasound probe has to have a large number of signal lines (generally, signal lines whose number corresponds to the number of the transducers).

Therefore, in the related art, a technique for reducing the number of the signal lines of the cable connecting the apparatus main body and the ultrasound probe has been proposed. For example, JP2012-152317A discloses an ultrasound probe including a plurality of switches that divide a transducer array of the ultrasound probe into an A group and a B group and switch a connection destination of a signal line from an apparatus main body to either a transducer in the A group or a transducer in the B group. According to this, one signal line from the apparatus main body can correspond to a plurality of transducers by the switching of the switch, so that the number of the signal lines of the cable can be reduced.

SUMMARY OF THE INVENTION

Incidentally, in the ultrasound probe, there is a demand for securing a large opening width in order to improve an azimuth resolution of the ultrasound image. Here, the opening width is a width in an arrangement direction of the transducer array, and specifically is the number of a group of transducers capable of simultaneously transmitting and receiving the ultrasonic wave among the transducers included in the transducer array.

For example, as in JP2012-152317A, in a case where the plurality of transducers included in the transducer array are divided into half (A group and B group) and the connection destination of the signal line from the apparatus main body is switched to either the transducer in the A group or the transducer in the B group, the maximum opening width is half the number of the transducers included in the transducer array.

In addition, in order to form a suitable ultrasound image, an opening of the ultrasound probe may be moved in the arrangement direction of the transducer array. For example, JP2012-152317A discloses that the transducer (a transducer that transmits and receives the ultrasonic wave) to which the signal line from the apparatus main body is connected is moved little by little in the arrangement direction of the transducer array. In the example of JP2012-152317A, in a case where the A group has 192 transducers of #1 to #192 and the B group has 192 transducers of #193 to #384, from a state where the transducers of #1 to #192 are connected to the apparatus main body, the switches are switched such that the transducer of #193 is connected to the apparatus main body instead of #1 and then the transducer of #194 is connected to the apparatus main body instead of #2. However, in order to perform such control, it is necessary to individually control the plurality of switches. Therefore, in this case, the cable connecting the apparatus main body and the ultrasound probe needs to have as many control signal lines as the number of the plurality of switches, and the number of the signal lines of the cable may not be reduced.

An object of the ultrasound probe disclosed in the present specification is to reduce the number of the signal lines connecting the ultrasound probe and the apparatus main body of the ultrasound diagnostic apparatus while suppressing reduction of the maximum opening width of the ultrasound probe.

An ultrasound probe disclosed in the present specification comprises: a transducer array consisting of a plurality of transducers that irradiate a subject with an ultrasonic wave and receive a reflected wave from the subject; and a connection circuit for electrically connecting an apparatus main body of an ultrasound diagnostic apparatus and the transducer array, in which the transducer array includes a plurality of main transducers arranged in a major axis direction and consisting of a plurality of center-side main transducers located on a center side of the arrangement, a plurality of first end-side main transducers located on a first end side of the arrangement with respect to the plurality of center-side main transducers, and a plurality of second end-side main transducers located on a second end side opposite to the first end side of the arrangement with respect to the plurality of center-side main transducers, and the connection circuit includes a first circuit connecting the apparatus main body and the center-side main transducer, and a second circuit having a plurality of main transducer switching switches for switching a connection destination of the apparatus main body between the first end-side main transducer and the second end-side main transducer.

In addition, each of the main transducer switching switches may switch the connection destination of the apparatus main body between a k-th first end-side main transducer from the first end side among the plurality of first end-side main transducers in the arrangement and a k-th second end-side main transducer from a side of the plurality of center-side main transducers among the plurality of second end-side main transducers.

With the configuration, the connection destination (a connection destination of one signal line included in a cable connecting the apparatus main body and the ultrasound probe) of the apparatus main body is switched between the first end-side main transducer and the second end-side main transducer by the second circuit. Therefore, the number of the signal lines of the cable can be reduced by the number of the first end-side main transducers or the second end-side main transducers.

Further, with the configuration, in a state where the apparatus main body and the first end-side main transducer are connected, the opening of the ultrasound probe is moved from the first end side toward the second end side, and in a case where a second end-side end portion of the opening reaches a second end-side end portion of the center-side main transducer, the connection destination of the apparatus main body can be controlled to be switched from the first end-side main transducer to the second end-side main transducer, and then the opening can be controlled to be moved to the second end side until it reaches a second end. As a result, the plurality of main transducer switching switches need only be controlled simultaneously, so that the reduction of the opening width of the ultrasound probe can be suppressed (the opening width is maintained at a width corresponding to the number of the center-side main transducers) while reducing the number of control signal lines (that is, the number of the signal lines of the cable) required to control the main transducer switching switches.

The first circuit may be provided on a first substrate, and the second circuit may be provided on a second substrate different from the first substrate.

With the configuration, the first substrate and the second substrate can be used for various ultrasound probes having various numbers of the transducers.

The transducer array may include a plurality of sub-transducers disposed on both sides of the respective main transducers in a minor axis direction orthogonal to the major axis direction, and the first circuit and the second circuit may each include a sub-transducer switching switch for switching between connection and non-connection between a signal line connected to the main transducer and the sub-transducers disposed on both sides of the main transducer in the minor axis direction.

With the configuration, the opening width in the minor axis direction can be switched.

An ultrasound diagnostic apparatus disclosed in the present specification comprises: the ultrasound probe according to claim 1, a transmission and reception circuit that transmits a transmission signal to the ultrasound probe, and that performs signal processing on a reception signal from the ultrasound probe; and a switch control circuit that controls switching of the main transducer switching switch, wherein, in a state in which the apparatus main body and the first end-side main transducer are connected to each other, the transmission and reception circuit transmits the transmission signal to the first end-side main transducer and the plurality of the center-side main transducers, and then moves an opening formed from a plurality of the main transducers which are targets of transmission of the transmission signal toward the second end side, the switch control circuit switches the main transducer switching switch so that the apparatus main body and the second end-side main transducer are connected to each other, when an end of the opening on the second end side has reached an end of the center-side main transducer on the second end side, and, in a state in which the apparatus main body and the second end-side main transducer are connected to each other, the transmission and reception circuit transmits the transmission signal to the plurality of the center-side main transducers and the second end-side main transducer, and then moves the opening toward the second end side.

The plurality of the first end-side main transducers may be divided into a plurality of first end-side blocks, each of which is a unit of switching control of the main transducer switching switch, and each including a plurality of the first end-side main transducers which are successive in the arrangement, the plurality of the second end-side transducers may be divided into a plurality of second end-side blocks, each of which is a unit of switching control of the main transducer switching switch, each corresponding respectively to each of the first end-side blocks according to the arrangement, and each including a plurality of the second end-side main transducers which are successive in the arrangement, in a state in which the apparatus main body and each of the first end-side blocks are connected to each other, the transmission and reception circuit may transmit the transmission signal to the first end-side block and some of the plurality of the center-side main transducers, and may then move an opening formed from a plurality of the main transducers which are targets of transmission of the transmission signal toward the second end side, the switch control circuit may switch the main transducer switching switch so that the apparatus main body is disconnected from a first end-side first block which is the first end-side block positioned at a position closest to the first end, and the apparatus main body and a second end-side first block which is the second end-side block adjacent to the center-side main transducer are connected to each other, when an end of the opening on the second end side has reached an end of the center-side main transducer on the second end side, and, in a state in which the apparatus main body is connected to the first end-side block(s) other than the first end-side first block and the second end-side first block, the transmission and reception circuit may transmit the transmission signal to the first end-side block(s) other than the first end-side first block, the plurality of the center-side main transducers, and a plurality of the second end-side main transducers included in the second end-side first block, and may then move the opening toward the second end side.

A maximum width APmax of the opening may be represented by: $APmax = USch - N$, wherein $USch = T - (B \times N)$, wherein T represents the number of the plurality of transducers, B represents the number of the first end-side blocks or the second end-side blocks, and N represents the number of transducers included in one first end-side block or one second end-side block.

With the ultrasound probe disclosed in the present specification, it is possible to reduce the number of the signal lines connecting the ultrasound probe and the apparatus main body of the ultrasound diagnostic apparatus while suppressing reduction of the maximum opening width of the ultrasound probe.

DESCRIPTION OF THE PREFERRED EMBODIMENTS

Figure 1:
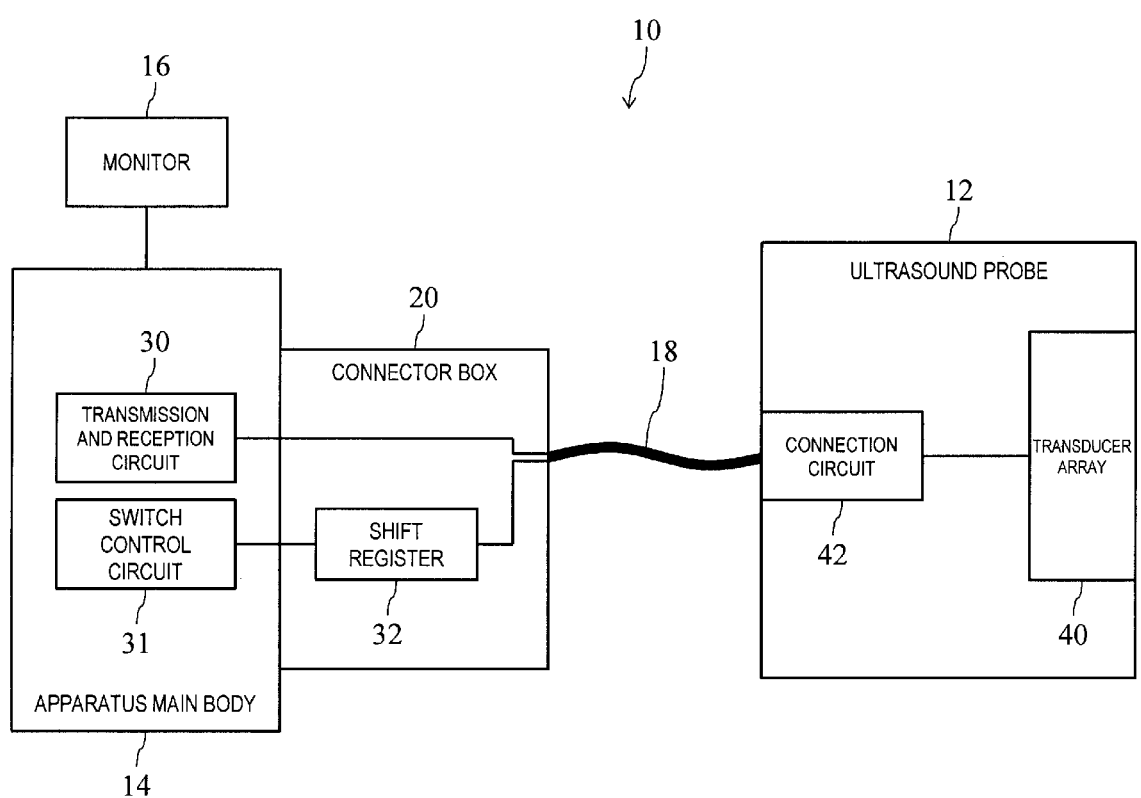
FIG. 1 is a block diagram of an ultrasound diagnostic apparatus according to the present embodiment.

<First Embodiment> FIG. 1 is a block diagram of an ultrasound diagnostic apparatus 10 according to the present embodiment. The ultrasound diagnostic apparatus 10 is a medical apparatus that is installed in a medical institution such as a hospital and that is used for an ultrasound examination.

The ultrasound diagnostic apparatus 10 is an apparatus that scans a subject with an ultrasonic beam and that generates an ultrasound image based on a reception signal obtained by the scanning. For example, the ultrasound diagnostic apparatus 10 forms a tomographic image (B-mode image) in which an amplitude intensity of a reflected wave from a scanning surface is converted into brightness based on the reception signal. Alternatively, the ultrasound diagnostic apparatus 10 forms a Doppler image, which is an ultrasound image representing a motion speed of a tissue in the subject, based on a difference (Doppler shift) in frequency between a transmission wave and a reception wave.

The ultrasound diagnostic apparatus 10 is configured to include an ultrasound probe 12, an apparatus main body 14, a monitor 16, a cable 18, and a connector box 20.

The ultrasound probe 12 is a device that transmits and receives an ultrasonic wave to and from the subject. Details of the ultrasound probe 12 will be described below.

The apparatus main body 14 is a device that performs a process of transmitting a transmission signal for causing the ultrasound probe 12 to transmit an ultrasonic wave, a process of forming an ultrasound image based on a reception signal from the ultrasound probe 12, or the like. Although the apparatus main body 14 includes various circuits for performing various processes, only a transmission and reception circuit 30 that transmits the transmission signal to the ultrasound probe 12 and performs signal processing on the reception signal from the ultrasound probe 12, and a switch control circuit 31 for controlling switching of a switch provided in a connection circuit 42, to be described later, are shown in FIG. 1.

The monitor 16 is composed of, for example, a liquid crystal display, an organic electro luminescence (EL), or the like. The ultrasound image formed by the apparatus main body 14 is displayed on the monitor 16.

The cable 18 electrically connects the ultrasound probe 12 and the apparatus main body 14. Specifically, the cable 18 has a plurality of signal lines, and each signal line connects each transducer included in a transducer array 40 of the ultrasound probe 12 and the transmission and reception circuit 30 of the apparatus main body 14. The connector box 20 is connected to the apparatus main body 14 side of the cable 18. By attaching the connector box 20 to a connector provided in the apparatus main body 14, the ultrasound probe 12 and the apparatus main body 14 are connected via the cable 18 and the connector box 20. In addition, as shown in FIG. 1, a shift register 32 is provided in the connector box 20. A function of the shift register 32 will be described below.

Hereinafter, the details of the ultrasound probe 12 will be described. The ultrasound probe 12 is configured to include the transducer array 40 and a connection circuit 42.

The transducer array 40 is composed of a plurality of transducers that irradiate the subject with an ultrasonic wave or receive a reflected wave from the subject.

Figure 2:
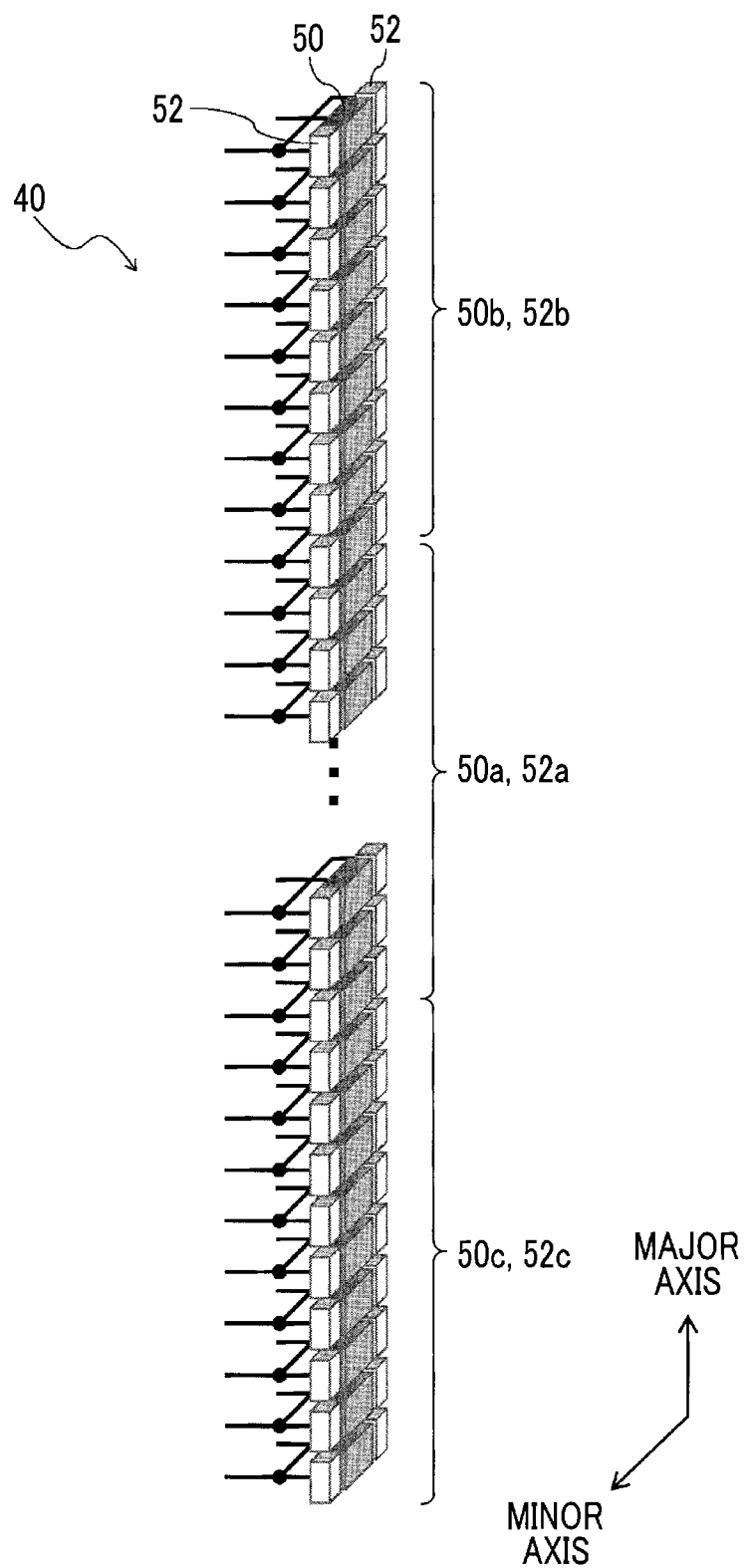
FIG. 2 is a schematic diagram of a transducer array.

FIG. 2 is a schematic diagram of the transducer array 40. The transducer array 40 is configured to include a plurality of main transducers 50 arranged in one direction. In the present specification, an arrangement direction of the main transducers 50 is referred to as a "major axis direction". The transducer array 40 is configured to include, for example, 320 main transducers 50, but the number of the main transducers 50 is not limited to this.

The plurality of main transducers 50 arranged in the major axis direction are conceptually divided into a plurality of center-side main transducers 50a located on a center side of the arrangement, a plurality of first end-side main transducers 50b located on a first end side (upper end side in FIG. 2) of the arrangement with respect to the plurality of center-side main transducers 50a, and a plurality of second end-side main transducers 50c located on a second end side (lower end side in FIG. 2) opposite to the first end side of the arrangement with respect to the plurality of center-side main transducers 50a. The number of the first end-side main transducers 50b is the same as the number of the second end-side main transducers 50c. The number of the center-side main transducers 50a and the number of the first end-side main transducers 50b or the number of the second end-side main transducers 50c may be the same as or different from each other.

In addition, in the present embodiment, the transducer array 40 is configured to include a plurality of sub-transducers 52 disposed on both sides of the respective main transducers 50 in a minor axis direction orthogonal to the major axis direction. The sub-transducer 52 exerts an effect of widening an opening in the minor axis direction. In the present embodiment, one sub-transducer 52 is provided on each of both sides of each main transducer 50 (two sub-transducers 52 for one main transducer 50), but the plurality of sub-transducers 52 may be provided on each of both sides of each main transducer 50.

As described above, since the plurality of main transducers 50 are arranged in the major axis direction, the plurality of sub-transducers 52 are also arranged in the major axis direction. The plurality of main transducers 50 include the center-side main transducers 50a, the first end-side main transducers 50b, and the second end-side main transducers 50c, and similarly, the plurality of sub-transducers 52 are also conceptually divided into a plurality of center-side sub-transducers 52a located on a center side of the arrangement, a plurality of first end-side sub-transducers 52b located on a first end side (upper end side in FIG. 2) of the arrangement with respect to the plurality of center-side sub-transducers 52a, and a plurality of second end-side sub-transducers 52c located on a second end side (lower end side in FIG. 2) opposite to the first end side of the arrangement with respect to the plurality of center-side sub-transducers 52a. The center-side sub-transducer 52a is disposed on both sides in the minor axis direction of the center-side main transducer 50a, the first end-side sub-transducer 52b is disposed on both sides in the minor axis direction of the first end-side main transducer 50b, and the second end-side sub-transducer 52c is disposed on both sides in the minor axis direction of the second end-side main transducer 50c.

In the present specification, the sub-transducers 52 disposed on both sides of the main transducer 50 in the minor axis direction may be described as the sub-transducers 52 corresponding to the (relevant) main transducer 50.

The connection circuit 42 is a circuit provided between the transmission and reception circuit 30 and the transducer array 40 in a signal path of a transmission signal from the transmission and reception circuit 30 (that is, the apparatus main body 14) and a reception signal from the transducer array 40, and is a circuit for electrically connecting the transmission and reception circuit 30 and the transducer array 40. Specifically, the connection circuit 42 is a circuit that electrically connects each transducer (the main transducer 50 and the sub-transducer 52) included in the transducer array 40 and the cable 18 (more specifically, each signal line included in the cable 18) connected to the transmission and reception circuit 30.

Figure 3:
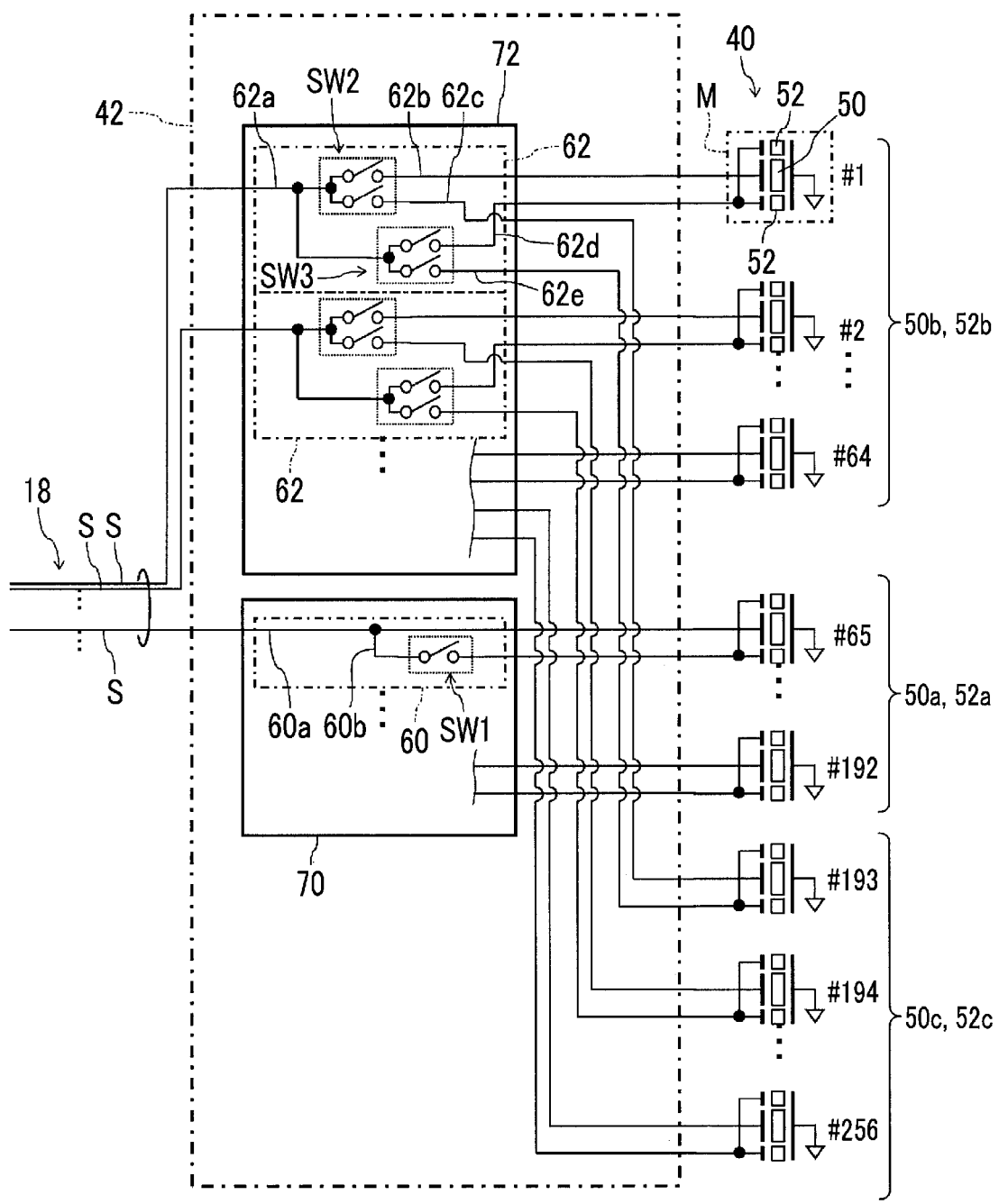
FIG. 3 is a circuit diagram of a connection circuit.

FIG. 3 is a circuit diagram of the connection circuit 42. Hereinafter, the connection circuit 42 will be described with reference to FIG. 3. In FIG. 3, on the right side of the connection circuit 42, the main transducer 50 and two sub-transducers 52 corresponding to the main transducer 50 are represented by one symbol M. A plurality of the symbols M arranged vertically represent the main transducers 50 and the sub-transducers 52 arranged in the major axis direction. A numerical value (#) described on the right side of each symbol M represents an order of the main transducer 50 or the sub-transducer 52 from the first end side in the arrangement. In the example of FIG. 3, 320 main transducers 50 are arranged in the major axis direction. In addition, in the example of FIG. 3, the number of the center-side main transducers 50a is 192 (#65 to #256), the number of the first end-side main transducers 50b is 64 (#1 to #64), and the number of the second end-side main transducers 50c is 64 (#257 to #320).

The connection circuit 42 is configured to include a first circuit 60 and a second circuit 62. The first circuit 60 is a circuit that connects the transmission and reception circuit 30 and the center-side main transducer 50a, and the second circuit 62 is a circuit having a function of switching a connection destination of the transmission and reception circuit 30 between the first end-side main transducer 50b and the second end-side main transducer 50c. Hereinafter, in the present specification, each signal path included in the first circuit 60 or the second circuit 62 will be referred to as a "pattern".

The first circuit 60 includes a main pattern 60a that connects the transmission and reception circuit 30 and the center-side main transducer 50a. Specifically, the main pattern 60a connects a transmission signal line S of the cable 18 and the center-side main transducer 50a. Therefore, as long as the connector box 20 is connected to the apparatus main body 14, the center-side main transducer 50a is always connected to the transmission and reception circuit 30 by the main pattern 60a.

In addition, the first circuit 60 includes a sub-pattern 60b that is branched from the main pattern 60a and is connected to the center-side sub-transducers 52a corresponding to the center-side main transducer 50a to which the main pattern 60a is connected. A switch SW1 as a sub-transducer switching switch is provided in the middle of the sub-pattern 60b. The switch SW1 is a switch for switching connection/non-connection between the main pattern 60a and the center-side sub-transducer 52a. In a case where the switch SW1 is ON, the center-side main transducer 50a and the center-side sub-transducers 52a corresponding to the center-side main transducer 50a are connected to the same main pattern 60a (that is, the same transmission signal line S). In a case where the switch SW1 is OFF, the center-side sub-transducer 52a is not connected to the main pattern 60a (that is, the transmission signal line S).

The first circuit 60 is provided for each center-side main transducer 50a (or center-side sub-transducers 52a corresponding to the center-side main transducer 50a).

The second circuit 62 includes a cable-side pattern 62a connected to the transmission signal line S of the cable 18, a first end-side main pattern 62b connected to the first end-side main transducer 50b, and a second end-side main pattern 62c connected to the second end-side main transducer 50c. A switch SW2 as a main transducer switching switch is provided between the cable-side pattern 62a, and the first end-side main pattern 62b and the second end-side main pattern 62c. The switch SW2 is a switch for switching a connection destination of the cable-side pattern 62a to either the first end-side main pattern 62b or the second end-side main pattern 62c. In other words, the connection destination of the transmission and reception circuit 30 is switched between the first end-side main transducer 50b and the second end-side main transducer 50c by the switch SW2.

Although the second circuit 62 is provided for each combination of one first end-side main transducer 50b and one second end-side main transducer 50c, the switch SW2 included in the second circuit 62 switches the connection destination of the transmission and reception circuit 30 between a k-th first end-side main transducer 50b from the first end side of the arrangement of the main transducers 50 and a k-th second end-side main transducer 50c from the center-side main transducer 50a side of the arrangement. For example, the switch SW2 of the 1st second circuit 62 switches the connection destination of the transmission and reception circuit 30 between the first end-side main transducer 50b which is the first (#1) in the arrangement of the plurality of main transducers 50 and the second end-side main transducer 50c which is the 257th (closest to the center-side main transducer 50a side (which may be referred to as the first end side of the arrangement) among the plurality of second end-side main transducers 50c) in the arrangement. In addition, the switch SW2 of the 2nd second circuit 62 switches the connection destination of the transmission and reception circuit 30 between the first end-side main transducer 50b which is the second (#2) in the arrangement of the plurality of main transducers 50 and the second end-side main transducer 50c which is the 258th (the second from the center-side main transducer 50a side (the first end side of the arrangement) among the plurality of second end-side main transducers 50c) in the arrangement.

In addition, the second circuit 62 includes a first end-side sub-pattern 62d connected to the first end-side sub-transducer 52b and a second end-side sub-pattern 62e connected to the second end-side sub-transducer 52c. A switch SW3 as a sub-transducer switching switch is provided between the cable-side pattern 62a, and the first end-side sub-pattern 62d and the second end-side sub-pattern 62e. The switch SW3 is a switch for switching a connection destination of the cable-side pattern 62a to either the first end-side sub-pattern 62d or the second end-side sub-pattern 62e. In other words, the connection destination of the transmission and reception circuit 30 is switched between the first end-side sub-transducer 52b and the second end-side sub-transducer 52c by the switch SW3.

As with the switch SW2, the switch SW3 included in one second circuit 62 switches the connection destination of the transmission and reception circuit 30 between a k-th first end-side sub-transducer 52b from the first end side of the arrangement of the sub-transducers 52 and a k-th second end-side sub-transducer 52c from the center-side sub-transducer 52a side of the arrangement. For example, the switch SW3 of the 1st second circuit 62 switches the connection destination of the transmission and reception circuit 30 between the first end-side sub-transducer 52b which is the first (#1) in the arrangement of the plurality of sub-transducers 52 and the second end-side sub-transducer 52c which is the 257th (closest to the center-side sub-transducer 52a side (which may be referred to as the first end side of the arrangement) among the plurality of second end-side sub-transducers 52c) in the arrangement. In addition, the switch SW3 of the 2nd second circuit 62 switches the connection destination of the transmission and reception circuit 30 between the first end-side sub-transducer 52b which is the second (#2) in the arrangement of the plurality of sub-transducers 52 and the second end-side sub-transducer 52c which is the 258th (the second from the center-side sub-transducer 52a side (the first end side of the arrangement) among the plurality of second end-side sub-transducers 52c) in the arrangement.

In the present embodiment, the connection circuit 42 is divided and provided on a plurality of substrates. Specifically, the first circuit 60 is provided on a first substrate 70, and the second circuit 62 is provided on a second substrate 72 different from the first substrate 70. In the present embodiment, the second circuit 62 is not provided on the first substrate 70, and the first circuit 60 is not provided on the second substrate 72.

For example, in the example of FIG. 3, the number of the provided center-side main transducers 50a is 192, so that 192 first circuits 60 are provided on the first substrate 70. A plurality of the first circuits 60 may be divided and provided on a plurality of the first substrates 70. For example, 96 first circuits 60 may be provided on the 1st first substrate 70, and 96 first circuits 60 may be provided on the 2nd first substrate 70. In this case, the ultrasound probe 12 is provided with two first substrates 70. The number of the first circuits 60 provided on one first substrate 70 may be appropriately determined.

In addition, in the example of FIG. 3, the number of the provided combinations of the first end-side main transducer 50b and the second end-side main transducer 50c are 64, so that 64 second circuits 62 are provided on the second substrate 72. A plurality of the second circuits 62 may be divided and provided on a plurality of the second substrates 72. For example, 32 second circuits 62 may be provided on the 1st second substrate 72, and 32 second circuits 62 may be provided on the 2nd second substrate 72. In this case, the ultrasound probe 12 is provided with two second substrates 72. The number of the second circuits 62 provided on one second substrate 72 may also be appropriately determined.

Figure 4:
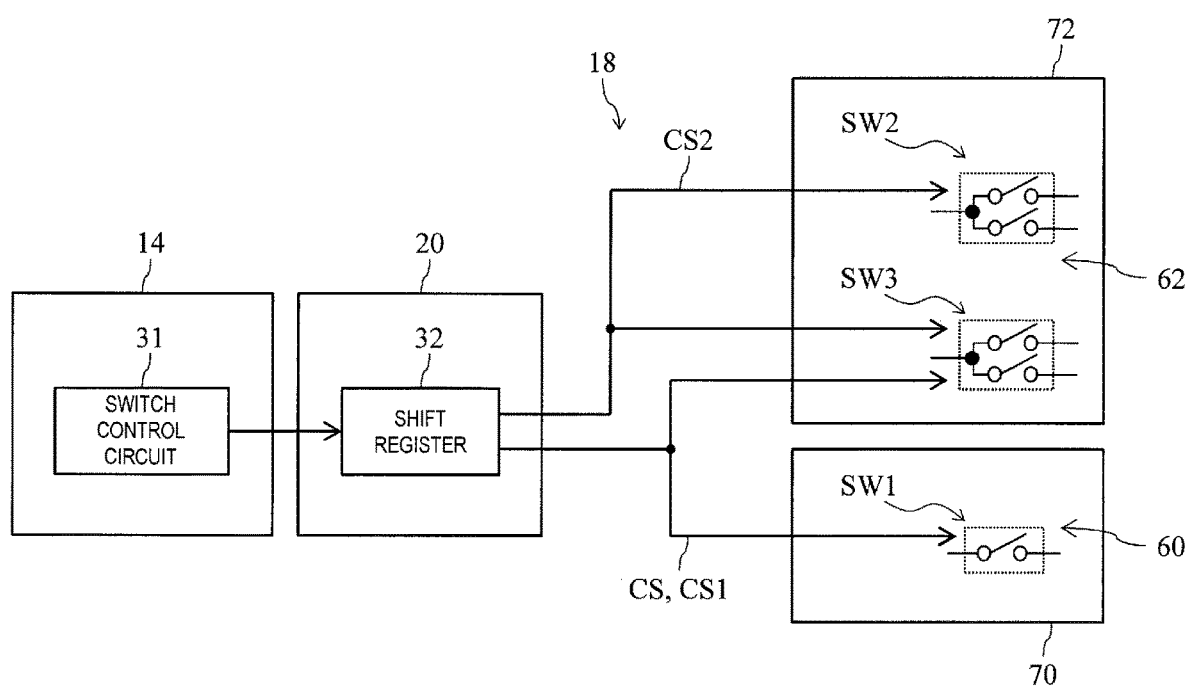
FIG. 4 is a circuit diagram of a control signal line for controlling each switch of the connection circuit in a first embodiment of the present disclosure.

FIG. 4 is a circuit diagram of a control signal line CS for controlling each switch (SW1, SW2, SW3) of the connection circuit 42. A control signal for controlling each switch is output from a switch control circuit 31. Note that a control signal of a dynamic signal is output to the shift register 32 from the switch control circuit 31, and the control signal is converted into a static signal by the shift register 32.

From the shift register 32, two control signal lines CS1 and CS2 are connected to the connection circuit 42 via the cable 18.

The control signal line CS1 is connected in parallel to a plurality of the switches SW1 included in the plurality of first circuits 60 provided on the first substrate 70 and a plurality of the switches SW3 included in the plurality of second circuits 62 provided on the second substrate 72. Accordingly, the control signal from the shift register 32 to the switches SW1 is supplied in parallel to the plurality of switches SW1 and the plurality of switches SW3. The switch SW1 is turned on in a case where a value of the control signal line CS1 is high (H), and the switch SW1 is turned off in a case where the value of the control signal line CS1 is low (L). The switch SW3 is enabled in a case where the value of the control signal line CS1 is H, and the switch SW3 is turned off in a case where the value of the control signal line CS1 is L. The state where the switch SW3 is enabled means a state where the cable-side pattern 62a is connected to either the first end-side sub-pattern 62d or the second end-side sub-pattern 62e. The state where the switch SW3 is turned off means a state where the cable-side pattern 62a is connected to neither the first end-side sub-pattern 62d nor the second end-side sub-pattern 62e.

In the present embodiment, the control signal line CS2 is connected in parallel to the plurality of switches SW2 and the plurality of switches SW3 included in the plurality of second circuits 62 provided on the second substrate 72. Accordingly, the control signal from the shift register 32 to the switches SW2 is supplied in parallel to the plurality of switches SW2. In a case where a value of the control signal line CS2 is L, the switch SW2 is in a state where the cable-side pattern 62a and the first end-side main pattern 62b are connected, and in a case where the value of the control signal line CS2 is H, the switch SW2 is in a state where the cable-side pattern 62a and the second end-side main pattern 62c are connected. That is, the plurality of switches SW2 included in the plurality of second circuits 62 are simultaneously controlled.

In the present embodiment, the control signal line CS2 is connected in parallel to the plurality of switches SW3. Accordingly, the control signal from the shift register 32 to the switches SW3 is supplied in parallel to the plurality of switches SW3. In a case where the value of the control signal line CS1 is H and the value of the control signal line CS2 is L, the switch SW3 is in a state where the cable-side pattern 62a and the first end-side sub-pattern 62d are connected, and in a case where the value of the control signal line CS1 is H and the value of the control signal line CS2 is H, the switch SW3 is in a state where the cable-side pattern 62a and the second end-side sub-pattern 62e are connected. That is, the plurality of switches SW3 included in the plurality of second circuits 62 are simultaneously controlled.

The outline of the ultrasound probe 12 according to the present embodiment is as described above. In the ultrasound probe 12, one transmission signal line S of the cable 18 corresponds to two main transducers 50 (the first end-side main transducer 50b and the second end-side main transducer 50c) by the second circuit 62, so that the number of the transmission signal lines S can be reduced by the number of the first end-side main transducers 50b (or the second end-side main transducers 50c).

In addition, in the arrangement direction of the main transducers 50, the connection destination of the transmission and reception circuit 30 is switched between the first end-side main transducers 50b and the second end-side main transducers 50c provided on both sides of the center-side main transducers 50a, whereby the reduction of the maximum opening width in the arrangement direction (major axis direction) of the main transducers 50 is suppressed. This will be described with reference to FIG. 5.

Figure 5:
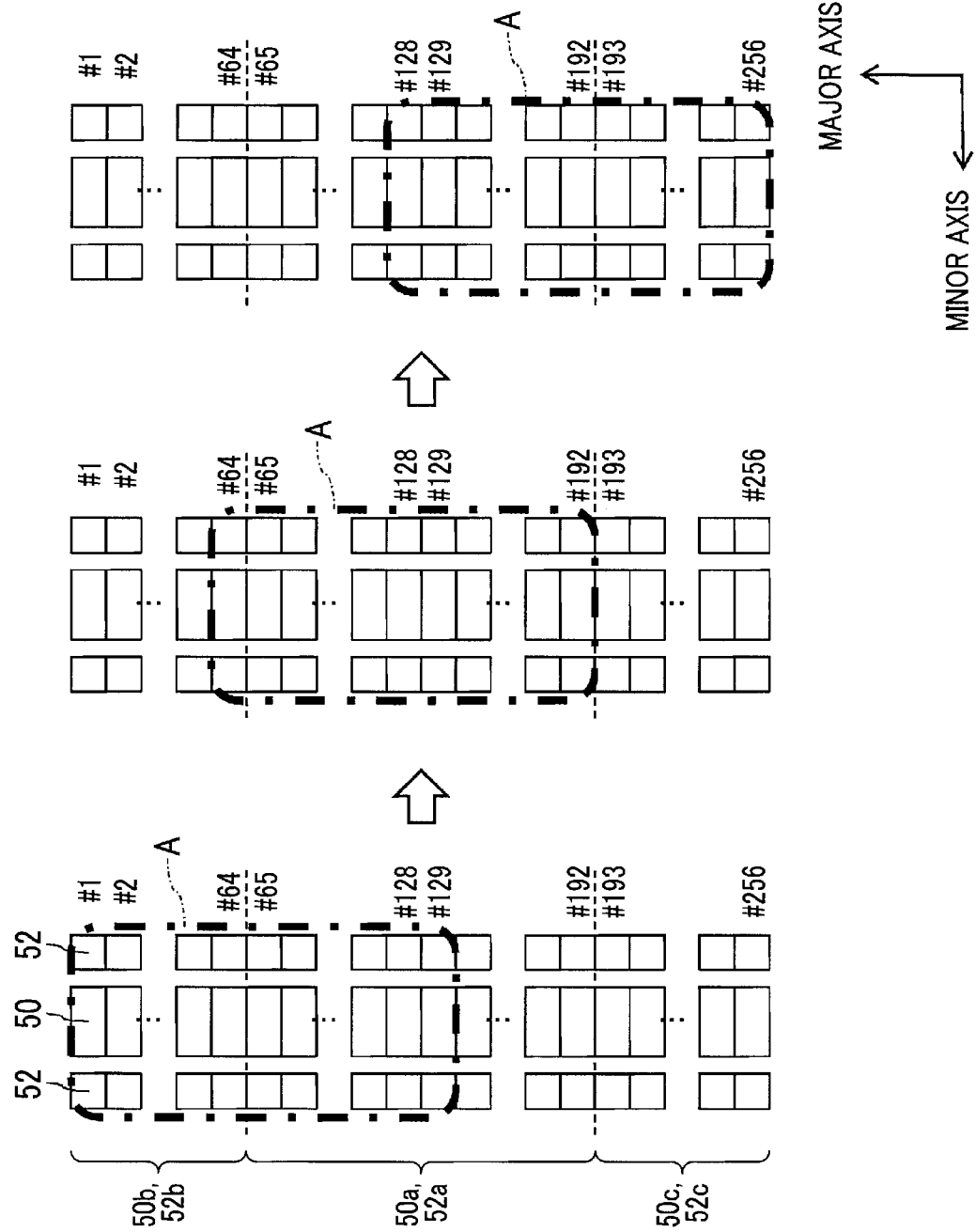
FIG. 5 is a diagram showing a state in which an opening of an ultrasound probe moves in the first embodiment of the present disclosure.

In the example of FIG. 5, an example is shown in which an opening A (corresponding to 160 transducers in the example of FIG. 5) with the maximum opening width is moved in a direction from the first end side to the second end side of the arrangement of the main transducers 50, that is, in a direction from the first (#1) to the 320th (#320) in the arrangement of the main transducers 50. Although FIG. 5 also shows the sub-transducer 52, the following description of the movement of the opening A in the major axis direction will be made with attention to the main transducer 50.

The figure on the left side of FIG. 5 shows a state where the opening A is the main transducers 50 of #1 to #160. In this case, the switch control circuit 31 controls the control signal line CS2 to L to connect the transmission and reception circuit 30 and the first end-side main transducers 50b (#1 to #64). In addition, the transmission and reception circuit 30 transmits a transmission signal to all of the first end-side main transducers 50b (#1 to #64) and a part of the center-side main transducers 50a (#65 to #160).

From this state, the transmission and reception circuit 30 gradually moves the opening A to the second end side (the side of the main transducer 50 of #320) of the arrangement of the main transducers 50 while maintaining the width of the opening A, while the switch control circuit 31 maintains the control signal line CS2 at L. That is, the transmission and reception circuit 30 gradually changes the main transducer 50 of a transmission destination of the transmission signal to the side of the main transducer 50 of #320. Eventually, an end of the opening A on the second end side reaches an end of the center-side main transducers 50a on the second end side, and the opening A becomes the main transducers 50 of #97 to #256 as shown in the middle figure of FIG. 5.

In this state, the switch control circuit 31 changes the control signal line CS2 to H and switches the connection destination of the transmission and reception circuit 30 from the first end-side main transducers 50b (#1 to #64) to the second end-side main transducers 50c (#257 to #320). Then, the transmission and reception circuit 30 transmits the transmission signal to some of the center-side main transducers 50a (#98 to #256) and the first of the second end-side main transducers 50c (#257).

Hereinafter, the transmission and reception circuit 30 gradually moves the opening A to the second end side (the side of the main transducer 50 #320) of the arrangement of the main transducers 50 while maintaining the width of the opening A, while the switch control circuit 31 maintains the control signal line CS2 at H. That is, the transmission and reception circuit 30 gradually changes the main transducer 50 of a transmission destination of the transmission signal to the side of the main transducer 50 #320. Eventually, the opening A becomes the main transducers 50 #161 to #320 as shown in the right figure in FIG. 5.

As described above, in the present embodiment, in the arrangement direction of the main transducers 50, the connection destination of the transmission and reception circuit 30 is switched between the first end-side main transducers 50b and the second end-side main transducers 50c provided on both sides of the center-side main transducers 50a, whereby reduction of the maximum width of the opening A can be suppressed. In addition, the plurality of switches SW2 for switching the connection destination of the transmission and reception circuit 30 between the first end-side main transducers 50b and the second end-side main transducers 50c need only be simultaneously controlled, so that the number of the control signal lines CS2 for switching the switches SW2 may be one. That is, according to the present embodiment, it is possible to reduce the number of the signal lines of the cable 18 while suppressing the reduction of the maximum opening width of the ultrasound probe 12.

In addition, in the present embodiment, the plurality of first circuits 60 are provided on the first substrate 70, and the plurality of second circuits 62 are provided on the second substrate 72. Accordingly, the first substrate 70 and the second substrate 72 can be used for various ultrasound probes 12 having various numbers of the transducers. For example, in a case where the first substrate 70 provided with 96 first circuits 60 and the second substrate 72 provided with 32 second circuits 62 are prepared, the ultrasound probe 12 having 320 transducers need only be provided with two first substrates 70 and two second substrates 72, the ultrasound probe 12 having 256 transducers need only be provided with two first substrates 70 and one second substrate 72, and the ultrasound probe 12 having 160 transducers need only be provided with one first substrate 70 and one second substrate 72.

In addition, in the present embodiment, by controlling the switch SW1, it is possible to also connect, to the transmission and reception circuit 30, the sub-transducers 52 corresponding to the main transducers 50 connected to the transmission and reception circuit 30. By switching the connection/non-connection of the transmission and reception circuit 30 to the sub-transducers 52, it becomes possible to vary an area for transmission and reception of the ultrasound, and to consequently adjust focus of the ultrasonic beam.

<Second Embodiment> A block diagram of an ultrasound diagnostic apparatus 10 according to a second embodiment of the present disclosure, a schematic diagram of the transducer array 40, and a circuit diagram of the connection circuit 42 are in the most part similar to those of the first embodiment of the present disclosure. The ultrasound diagnostic apparatus 10 according to the second embodiment will now be described primarily with regard to portions that are different from the first embodiment.

Figure 6:
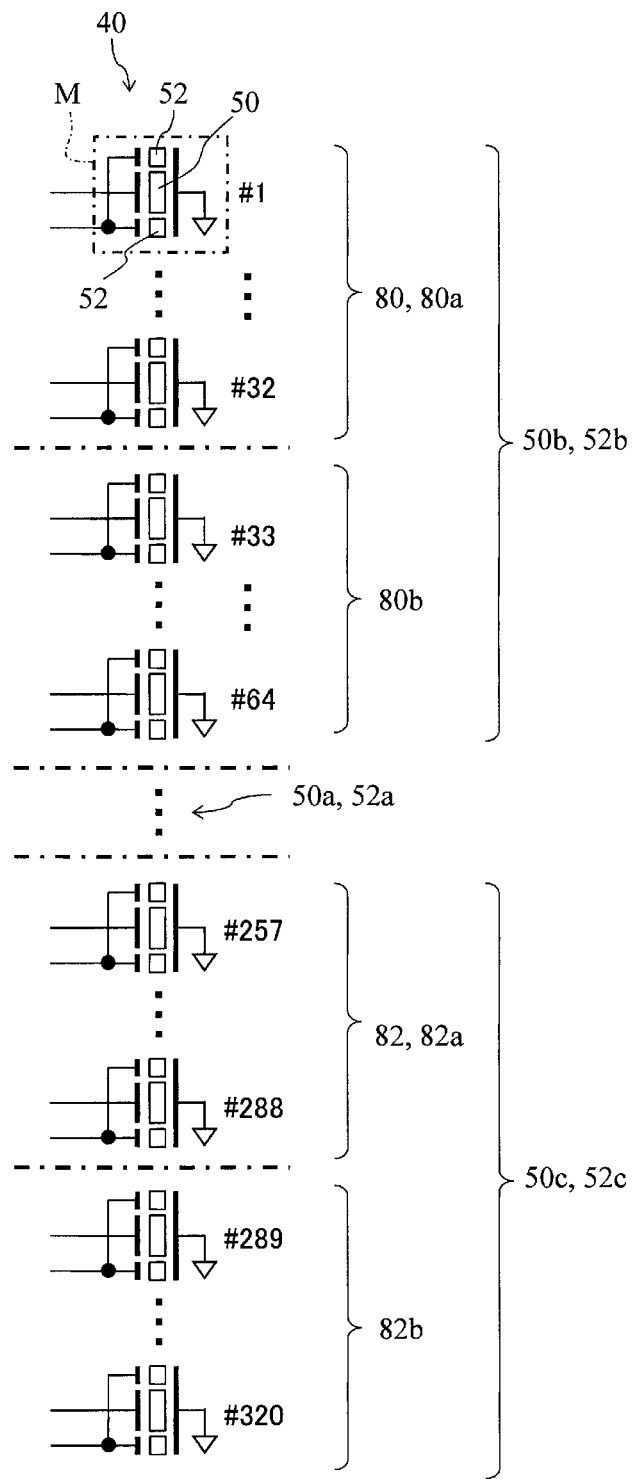
FIG. 6 is a conceptual diagram showing a plurality of first end-side blocks and a plurality of second end-side blocks in a second embodiment of the present disclosure.

FIG. 6 is a conceptual diagram showing a plurality of first end-side blocks 80 and a plurality of second end-side blocks 82 defined in the transducer array 40. In the second embodiment, the plurality of the first end-side main transducers 50b are conceptually divided into the plurality of first end-side blocks 80. Each first end-side block 80 also includes a plurality of the first end-side sub-transducers 52b, but in the following, description will be given with attention to the main transducers 50, and the sub-transducers 52 will be described later. Each first end-side block 80 is formed including a plurality of first end-side transducers 50b which are successive in the arrangement of the transducer array 40. In the present embodiment, as shown in FIG. 6, the first end-side blocks 80 are divided into two first end-side blocks 80, including a first end-side first block 80a including the first end-side main transducers 50b of #1 to #32, and a first end-side second block 80b including the first end-side main transducers 50b of #33 to #64. In this manner, in the present embodiment, each first end-side block 80 includes 32 first end-side main transducers 50b. The number of the first end-side blocks 80 is not limited to two, and may be another number. As will be described later in detail, the first end-side block 80 is a unit for performing switching control of the switch SW2 serving as the main transducer switching switch.

Similarly, in the second embodiment, the plurality of the second end-side main transducers 50*c* are conceptually divided into a plurality of second end-side blocks 82. Similar to the first end-side block 80, each second end-side block 82 also includes a plurality of the second end-side sub-transducers 52*c*, but in the following, description will be given with attention to the main transducers 50, and the sub-transducers 52 will be described later. Each second end-side block 82 is also formed including a plurality of the second end-side main transducers 50*c* which are successive in the arrangement of the transducer array 40. In the present embodiment, as shown in FIG. 6, the second end-side blocks 82 are divided into two second end-side blocks 82 including a second end-side first block 82*a* including the second end-side main transducers 50*c* #257 to #288, and a second end-side second block 82*b* including the second end-side main transducers 50*c* #289 to #320. In this manner, in the present embodiment, each second end-side block 82 includes 32 second end-side main transducers 50*c*. In particular, each second end-side block 82 is provided corresponding to each first end-side block 80, according to the arrangement of the transducer array 40. In the present embodiment, a second end-side first block 82*a* positioned at the closest position to the first end among the second end-side blocks 82 (that is, adjacent to the center-side main transducer 50*a*) corresponds to the first end-side first block 80*a* which is positioned at the closest position to the first end among the first end-side blocks 80. In addition, a second end-side second block 82*b* which is at the second position from the first end side among the second end-side blocks 82 corresponds to a first end-side second block 80*b* at the second position from the first end side among the first end-side blocks 80. In this manner, the number of the first end-side blocks 80 and the number of the second end-side blocks 82 are equal to each other. In addition, the number of the first end-side main transducers 50*b* included in the first end-side block 80 and the number of the second end-side main transduces 50*c* included in the second end-side block 82 corresponding to the first end-side block 80 are equal to each other. The second end-side block 82 is also a unit for performing the switching control of the switch SW2.

Figure 7:
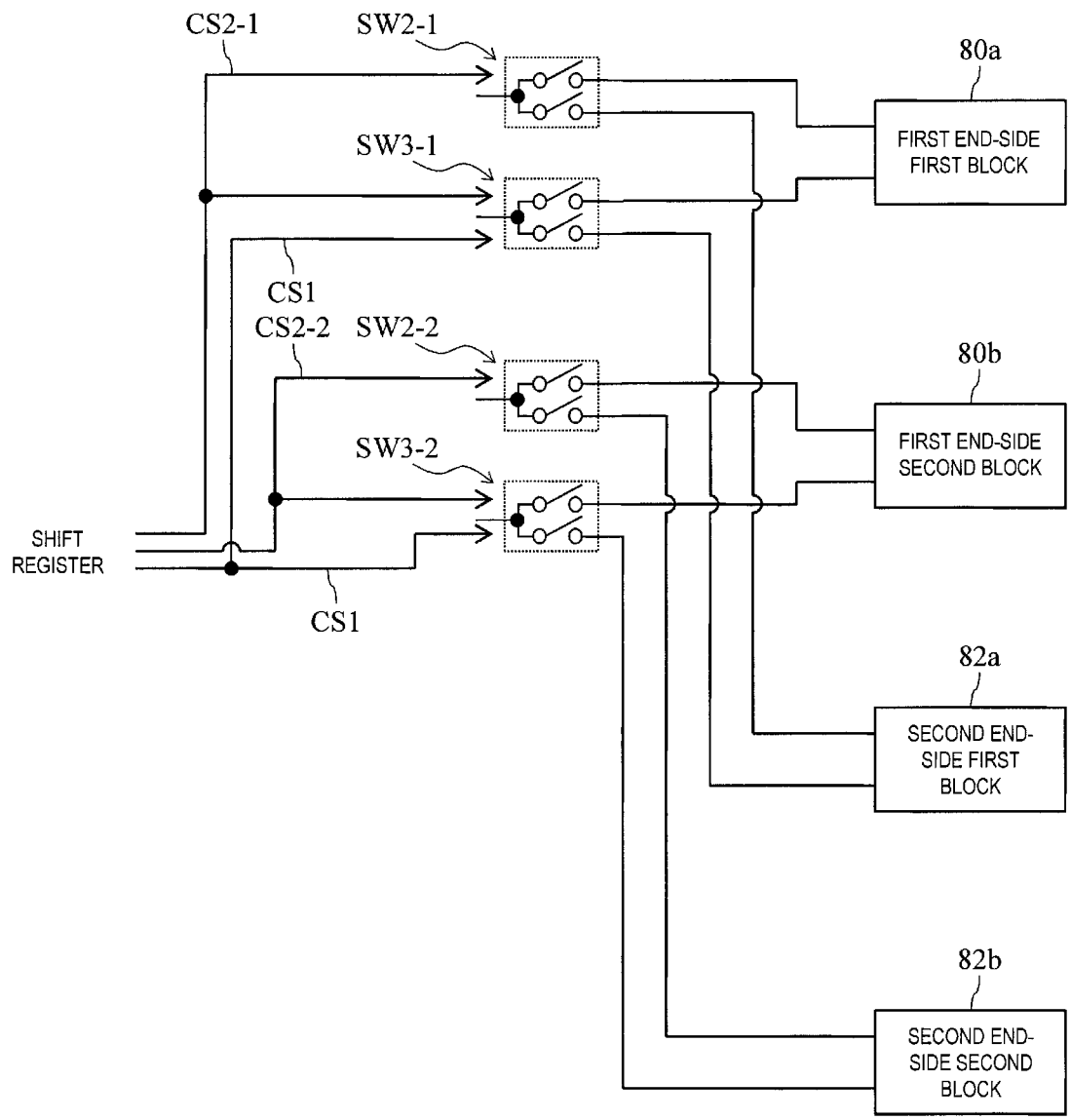
FIG. 7 is a circuit diagram showing a connection relationship among a first end-side block, a second end-side block, a switch provided in a connection circuit, and a control signal line for controlling the switch, in the second embodiment of the present disclosure.

FIG. 7 is a circuit diagram showing a connection relationship among the first end-side block 80, the second end-side block 82, the switches SW2 and SW3, the control signal line CS1, and the control signal line CS2 for controlling the switches SW2 and SW3. In the second embodiment also, a switch SW1 (refer to FIG. 4), to which the plurality of center-side main transducers 50*a* (and the plurality of center-side sub-transducers 52*a*) and the control signal line CS1 are connected, is provided, but illustration thereof is omitted in FIG. 7.

Similar to the first embodiment, the switch SW2 changes the connection destination of the transmission and reception circuit 30 (refer to FIG. 1) between the first end-side main transducer 50*b* and the second end-side main transducer 50*c*. In particular, in the second embodiment, the switch SW2 switches the connection destination of the transmission and reception circuit 30 between a first end-side main transducer 50*b* included in the first end-side block 80, and a second end-side main transducer 50*c* included in the second end-side block 82 corresponding to the first end-side block 80. In the example configuration of FIG. 7, a switch SW2-1 switches between a first end-side main transducer 50*b* included in the first end-side first block 80*a*, and a second end-side main transducer 50*c* included in the second end-side first block 82*a*, and a switch SW2-2 switches between a first end-side main transducer 50*b* included in the first end-side second block 80*b* and a second end-side main transducer 50*c* included in the second end-side second block 82*b*. While the example configuration of FIG. 7 only shows one switch SW2 for one set of the first end-side block 80 and the second end-side block 82 (for example, only one switch SW2-1 is shown for the set of the first end-side first block 80*a* and the second end-side first block 82*a*), in reality, the switches SW2 for the set are provided in a number corresponding to the number of the main transducers 50 included in the first end-side block 80 and the second end-side block 82. In the present specification, a plurality of switches SW2 for the set of the first end-side first block 80*a* and the second end-side first block 82*b* will be collectively referred to as the "switch SW2-1", and a plurality of switches SW2 for the set of the first end-side second block 80*b* and the second end-side second block 82*b* will be collectively referred to as the "switch SW2-2".

In the first embodiment, one control signal line CS2 is connected in parallel to a plurality of switches SW2 and a plurality of switches SW3. That is, switching of all of the switches SW2 and all of the switches SW3 are simultaneously controlled. On the other hand, in the second embodiment, separate control signal lines CS2 are provided respectively for the plurality of switches SW2 corresponding to a plurality of sets of the first end-side blocks 80 and the second end-side blocks 82. In the example configuration of FIG. 7, a control signal line CS2-1 for transmitting the control signal from the shift register 32 to the switch SW2-1 for the set of the first end-side first block 80*a* and the second end-side first block 82*a* is provided, and a control signal line CS2-2 for transmitting the control signal from the shift register 32 to the switch SW2-2 for the set of the first end-side second block 80*b* and the second end-side second block 82*b* is provided. With this configuration, in the second embodiment, the switches SW2 corresponding to the respective sets of the first end-side blocks 80 and the second end-side blocks 82 can be individually controlled. That is, in the second embodiment, the connection destination of the transmission and reception circuit 30 can be switched individually for each set of the first end-side block 80 and the second end-side block 82.

In the present embodiment, when the value of the control signal line CS2-1 is L, the switch SW2-1 is set to a state in which the transmission and reception circuit 30*a* and the first end-side main transducers 50*b* included in the first end-side first block 80*a* are connected to each other, and, when the value of the control signal line CS2-1 is H, the switch SW2-1 is set to a state in which the transmission and reception circuit 30*a* and the second end-side main transducers 50*c* included in the second end-side first block 82*a* are connected to each other. Similarly, in the present embodiment, when the value of the control signal line CS2-2 is L, the switch SW2-2 is set to a state in which the transmission and reception circuit 30*a* and the first end-side main transducers 50*b* included in the first end-side second block 80*b* are connected to each other, and, when the value of the control signal line CS2-2 is H, the switch SW2-2 is set to a state in which the transmission and reception circuit 30*a* and the second end-side main transducers 50*c* included in the second end-side second block 82*b* are connected to each other.

The switching control of the switch SW2 and the transmission control of the transmission signal for moving the opening A in the major axis direction in the second embodiment will now be described with reference to FIG. 8. FIG.

8 also shows the sub-transducers 52, but the description will be given with attention to the main transducers 50.

Figure 8:
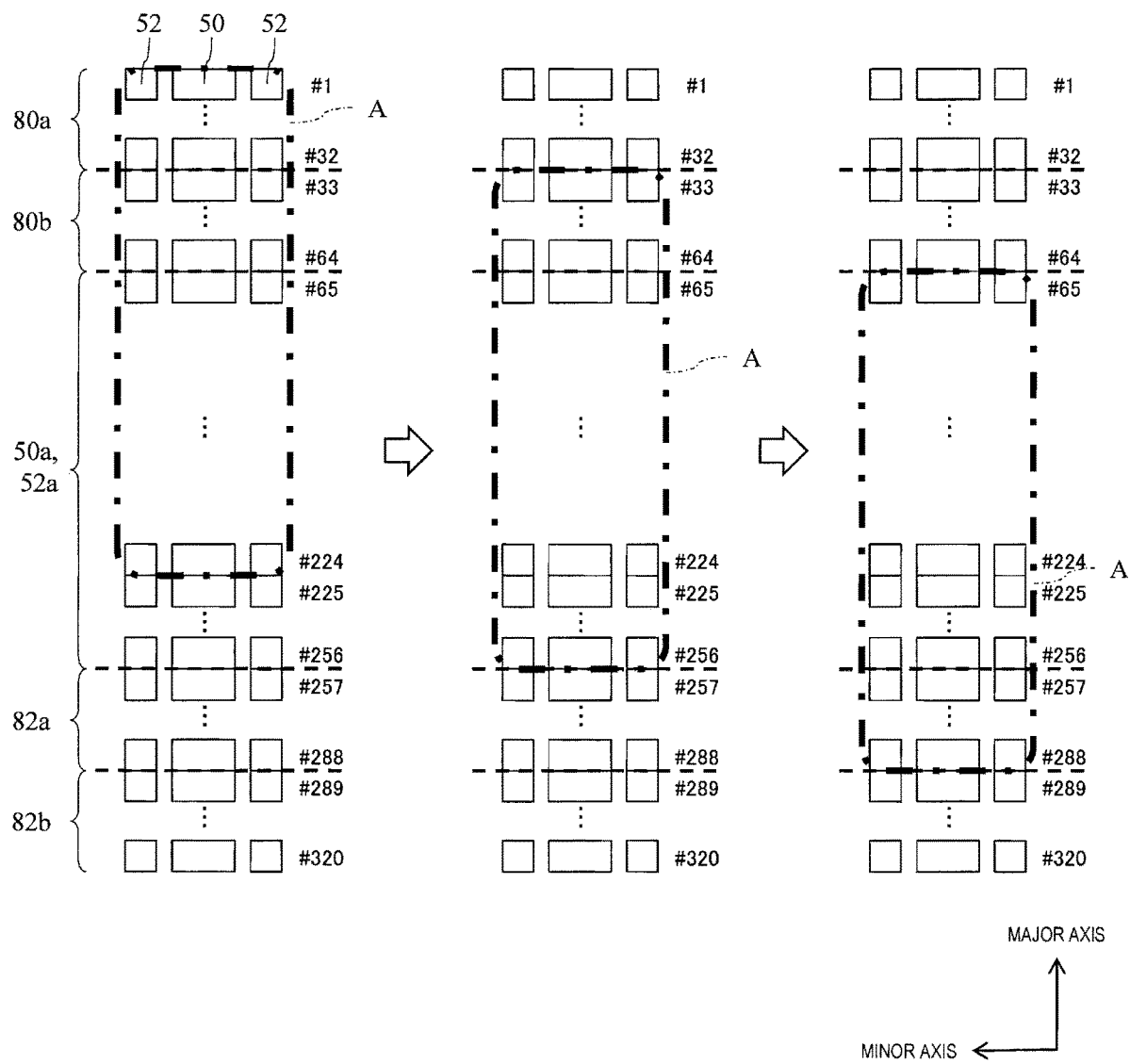
FIG. 8 is a diagram showing a state in which an opening of an ultrasound probe moves in the second embodiment of the present disclosure.

The figure on the left side of FIG. 8 shows a state where the opening A is the main transducers 50 #1 to #224. As will be described later in detail, when the number of the main transducers 50 is 320, the number of the first end-side blocks 80 (or the second end-side blocks 82) is 2, and the number of the main transducers 50 included in each first end-side block 80 (or each second end-side block 82) is 32, the maximum opening width is a width corresponding to 224 main transducers 50, as shown in FIG. 8.

When the opening A is the main transducers 50 #1 to #224, the switch control circuit 31 controls the control signal lines CS2-1 and CS2-2 to L to connect the transmission and reception circuit 30 and the first end-side main transducers 50b (#1 to #64) included in first end-side blocks 80 (that is, the first end-side first block 80a and the first end-side second block 80b). In this state, the transmission and reception circuit 30 transmits the transmission signal to all of the plurality of the first end-side main transducers 50b (#1 to #64) included in the first end-side blocks 80 and some of the plurality of the center-side main transducers 50a (#65 to #224).

From this state, the transmission and reception circuit 30 gradually moves the opening A to the second end side (the side of the main transducer 50 of #320) of the arrangement of the main transducers 50 while maintaining the width of the opening A, while the switch control circuit 31 maintains the control signal lines CS2-1 and CS2-2 at L. That is, the transmission and reception circuit 30 gradually changes the main transducer 50 of a transmission destination of the transmission signal to the side of the main transducer 50 #320. Eventually, an end of the opening A on the second end side reaches an end of the center-side main transducers 50a on the second end side, and the opening A becomes the main transducers 50 #33 to #256 as shown in the middle figure of FIG. 8.

In this state, the switch control circuit 31 changes the control signal line CS2-1 to H while maintaining the control signal line CS2-2 at L. With this process, the transmission and reception circuit 30 is disconnected from the first end-side main transducers 50b (#1 to #32) included in the first end-side first block 80a, and instead, the transmission and reception circuit 30 and the second end-side main transducers 50c (#257 to #288) included in the second end-side first block 82a are connected to each other. In this state, the connection destination of the transmission and reception circuit 30 is the first end-side main transducers 50b (#33 to #64) included in the first end-side second block 80b, the center-side main transducers 50a (#65 to #256), and the second end-side main transducers 50c (#257 to #288) included in the second end-side first block 82a.

In this state, the transmission and reception circuit 30 transmits the transmission signal to some of the first end-side main transducers 50b (#34 to #64) included in the first end-side block(s) 80 other than the first end-side first block 80a (in the present example configuration, the first end-side second block 80b), all of the plurality of the center-side main transducers 50a, and the first of the second end-side main transducers 50c (#257) included in the second end-side first block 82a.

Then, the transmission and reception circuit 30 gradually moves the opening A to the second end side (the side of the main transducer 50 #320) of the arrangement of the main transducers 50 while maintaining the width of the opening A, while the switch control circuit 31 maintains the control signal line CS2-1 at H and the control signal line CS2-2 at L. Eventually, an end of the opening A on the second end side reaches an end of the second end-side first block 82a on the second end side, and the opening A becomes the main transducers 50 #65 to #288 as shown in the right figure of FIG. 8.

In this state, the switch control circuit 31 changes the control signal line CS2-2 to L while maintaining the control signal line CS2-1 at H. With this process, the transmission and reception circuit 30 is disconnected from the first end-side main transducers 50b (#33 to #64) included in the first end-side second block 80b, and instead, the transmission and reception circuit 30 and the second end-side main transducers 50c (#289 to #320) included in the second end-side second block 82b are connected to each other. In this state, the connection destination of the transmission and reception circuit 30 is the center-side main transducers 50a (#65 to #256), and the second end-side main transducers 50c (#257 to #320) included in the second end-side blocks 82 (that is, the second end-side first block 82a and the second end-side second block 82b).

In this state, the transmission and reception circuit 30 transmits the transmission signal to some of the plurality of the center-side main transducers 50a (#66 to #256), all of the second end-side main transducers 50c included in the second end-side first block 82a (#257 to #288), and the first of the second end-side main transducers 50c (#289) included in the second end-side second block 82b.

Then, the transmission and reception circuit 30 gradually moves the opening A to the second end side (the side of the main transducer 50 #320) of the arrangement of the main transducers 50 while maintaining the width of the opening A, while the switch control circuit 31 maintains the control signal lines CS2-1 and CS2-2 at H. Eventually, an end of the opening A on the second end side reaches an end of the second end-side second block 82b on the second end side (in the present embodiment, an end of the transducer array 40 on the second end side), and the opening A becomes the main transducers 50 #97 to #320.

As described, in the second embodiment, the plurality of the first end-side main transducers 50b are divided into a plurality of the first end-side blocks 80, the plurality of the second end-side main transducers 50c are divided into a plurality of the second end-side blocks 82, and, for each set of the first end-side block 80 and the second end-side block 82, the opening A is moved while the connection destination of the transmission and reception circuit 30 is sequentially switched. In the embodiment described above, a configuration is described in which the numbers of the first end-side blocks 80 and the second end-side blocks 82 are 2, but the case in which the numbers of the first end-side blocks 80 and the second end-side blocks 82 are three or more can be similarly handled, and, for each set of the first end-side block 80 and the second end-side block 82, the opening A is moved while the connection destination of the transmission and reception circuit 30 is sequentially switched.

In the second embodiment, with the above-described process, the opening width of the opening A may be widened at least in comparison to the first embodiment. Specifically, a maximum width APmax of the opening A is represented by the following Equation 1.

$$APmax = USch - N \quad \text{(Equation 1)}$$

In Equation 1, USch (which is referred to as an "apparatus channel" in the present specification) indicates the number of a plurality of main transducers 50 which can be connected simultaneously to the transmission and reception circuit 30, and is represented by the following Equation 2.

$$USch = T - (B \times N) \quad \text{(Equation 2)}$$

In Equation 2, T represents the number of the plurality of main transducers 50 included in the transducer array 40, B represents the number of the first end-side blocks 80 or the second end-side blocks 82, and N represents the number of the main transducers 50 included in one first end-side block 80 or one second end-side block 82.

In the present embodiment, T=320, B=2, and N=32, and USch is thus 256. Therefore, the maximum width APmax of the opening A in the present embodiment is 256−32=224.

Figure 9:
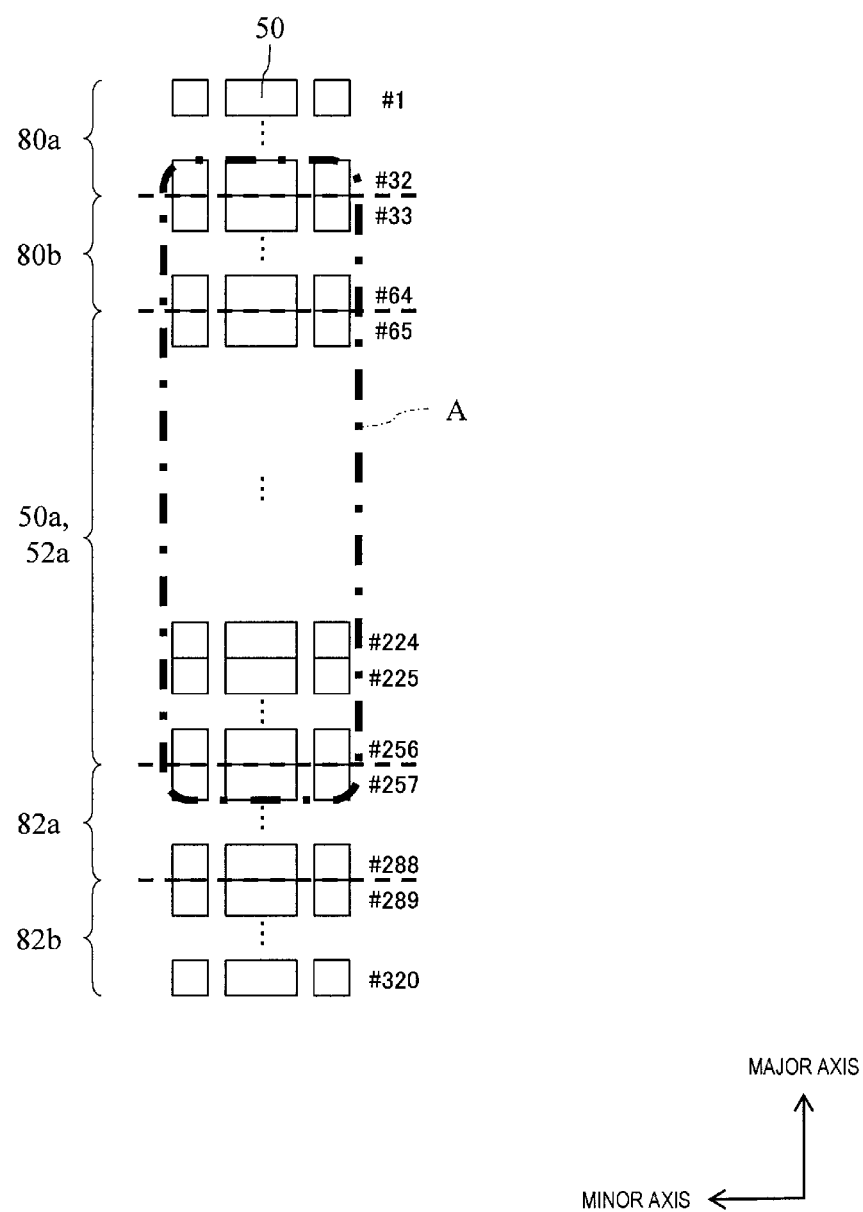
FIG. 9 is a diagram showing the opening when a maximum width of the opening is set larger than USch–N.

If the maximum width APmax of the opening A is set larger than USch−N, as shown in FIG. 9, when the end of the opening A on the second end side enters the second end-side first block 82a, an end of the opening A on the first end side would remain in the first end-side first block 80a. As described above, the first end-side first block 80a and the second end-side first block 82a are exclusively connected to the transmission and reception circuit 30. Thus, in this case, it becomes impossible to transmit the transmission signal to either the first end-side main transducer 50b included in the first end-side first block 80a or the second end-side main transducer 50c included in the second end-side first block 82a. In the example configuration of FIG. 9, the transmission signal cannot be transmitted to #32 or #257 either. In order to avoid such a situation, in the present embodiment, a value obtained by subtracting the number of the main transducers 50 in one block from the apparatus channel USch is set as the maximum width APmax of the opening A.

Further, in the second embodiment, a number Cn of the signal lines of the cable 18 is USch (number of transmission signal lines S)+B (number of the control signal lines CS2)+1 (the control signal line CS1). If the transducer array 40 does not include the sub-transducers 52, the number Cn of the signal lines of the cable 18 is USch (number of the transmission signal lines S)+B (number of the control signal lines CS2).

Next, the sub-transducers 52 in the second embodiment will be described. As shown in FIG. 6, each first end-side block 80 includes the first end-side sub-transducers 52b corresponding to the first end-side main transducers 50b included therein, and each second end-side block 82 includes the second end-side sub-transducers 52c corresponding to the second end-side main transducers 50c included therein. That is, conceptually, the plurality of the first end-side sub-transducers 52b are also divided into the plurality of the first end-side blocks 80, and, conceptually, the plurality of the second end-side sub-transducers 52c are also divided into the plurality of the second end-side blocks 82.

As shown in FIG. 7, in the second embodiment, the switch SW3 switches the connection destination of the transmission and reception circuit 30 between the first end-side sub-transducers 52b included in the first end-side block 80, and the second end-side sub-transducers 52c included in the second end-side block 82 corresponding to the first end-side block 80. In the example configuration of FIG. 7, a switch SW3-1 switches between the first end-side sub-transducers 52b included in the first end-side first block 80a and the second end-side sub-transducers 52c included in the second end-side first block 82a, and a switch SW3-2 switches between the first end-side sub-transducers 52b included in the first end-side second block 80b and the second end-side sub-transducers 52c included in the second end-side second block 82b. While the example configuration of FIG. 7 only shows one switch SW3 for one set of the first end-side block 80 and the second end-side block 82 (for example, only one switch SW3-1 is shown for the set of the first end-side first block 80a and the second end-side first block 82a), in reality, the switches SW3 for the set are provided in a number corresponding to the number of pairs of the sub-transducers 52 included in the first end-side blocks 80 and the second end-side blocks 82. In the present specification, a plurality of switches SW3 for the set of the first end-side first block 80a and the second end-side first block 82a will be collectively referred to as the "switch SW3-1", and a plurality of switches SW3 for the set of the first end-side second block 80b and the second end-side second block 82b will be collectively referred to as the "switch SW3-2".

In the second embodiment also, similar to the first embodiment, the control signal line CS1 is connected in parallel to the plurality of the switches SW3. When the value of the control signal line CS1 is H, the switch SW3 is enabled, and when the value of the control signal line CS1 is L, the switch SW3 is turned off.

In such a structure, the focus of the ultrasonic beam can be adjusted by suitably controlling the control signal line CS1, similar to the first embodiment.

For example, in the state shown in the figure on the left side of FIG. 8, that is, in a state in which the switch control circuit 31 controls the control signal lines CS2-1 and CS2-2 to L, and the transmission and reception circuit 30 is connected to the first end-side main transducers 50b (#1 to #64) included in the first end-side block 80, and the center-side main transducers 50a (#65 to #256), when the switch control circuit 31 changes the control signal line CS1 from L to H, the switch SW3-1, the switch SW3-2, and the switch SW1 (refer to FIG. 4) are turned on, and the first end-side sub-transducers 52b included in the first end-side block 80 and the center-side sub-transducers 52a are connected to the transmission and reception circuit 30. In this state, the transmission and reception circuit 30 can transmit the transmission signal to the first end-side sub-transducers 52b included in the first end-side block 80 and the center-side sub-transducers 52a, and can receive reception signals from the first end-side sub-transducers 52b included in the first end-side block 80 and the center-side sub-transducers 52a.

In the state in which the switch control circuit 31 controls the control signal line CS2-1 to H and the control signal line CS2-2 to L, and the transmission and reception circuit 30 is connected to the first end-side main transducers 50b (#33 to #64) included in the first end-side second block 80b, the center-side main transducers 50a (#65 to #256), and the second end-side main transducers 50c (#257 to #288) included in the second end-side first block 82a, when the switch control circuit 31 changes the control signal line CS1 from L to H, the switch SW1, the switch SW3-1, and the switch SW3-2 are turned on, and the first end-side sub-transducers 52b included in the first end-side second block 80b, the center-side sub-transducers 52a, and the second end-side sub-transducers 52c included in the second end-side first block 82a are connected to the transmission and reception circuit 30. In this state, the transmission and reception circuit 30 can transmit the transmission signal to the first end-side sub-transducers 52b included in the first end-side second block 80b, the center-side sub-transducers 52a, and the second end-side sub-transducers 52c included in the second end-side first block 82a, and can receive reception signals from the first end-side sub-transducers 52b included in the first end-side second block 80b, the center-side sub-transducers 52a, and the second end-side sub-transducers 52c included in the second end-side first block 82a.

Further, in the state in which the switch control circuit 31 controls the control signal lines CS2-1 and CS2-2 to H, and the transmission and reception circuit 30 is connected to the center-side main transducers 50a (#65 to #256), and the second end-side main transducers 50c (#257 to #320) included in the second end-side block 82, when the switch control circuit 31 changes the control signal line CS1 from L to H, the switch SW1, the switch SW3-1, and the switch SW3-2 are turned on, and the center-side sub-transducers 52a and the second end-side sub-transducers 52c included in the second end-side block 82 are connected to the transmission and reception circuit 30. In this state, the transmission and reception circuit 30 can transmit the transmission signal to the center-side sub-transducers 52a, and the second end-side sub-transducers 52c included in the second end-side block 82, and can receive reception signals from the center-side sub-transducers 52a and the second end-side sub-transducers 52c included in the second end-side block 82.

Although the embodiment according to the present invention has been described above, the present invention is not limited to the above-described embodiment, and various changes can be made without departing from the spirit of the present invention.

EXPLANATION OF REFERENCES

10: ultrasound diagnostic apparatus
12: ultrasound probe
14: apparatus main body
16: monitor
18: cable
20: connector box
30: transmission and reception circuit
31: switch control circuit
32: shift register
40: transducer array
42: connection circuit
50: main transducer
50a: center-side main transducer
50b: first end-side main transducer
50c: second end-side main transducer
52: sub-transducer
52a: center-side sub-transducer
52b: first end-side sub-transducer
52c: second end-side sub-transducer
60: first circuit
60a: main pattern
60b: sub-pattern
62: second circuit
62a: cable-side pattern
62b: first end-side main pattern
62c: second end-side main pattern
62d: first end-side sub-pattern
62e: second end-side sub-pattern
70: first substrate
72: second substrate
80: first end-side block
80a: first end-side first block
80b: first end-side second block
82: second end-side block
82a: second end-side first block
82b: second end-side second block
S: signal line
SW1, SW2, SW2-1, SW2-2, SW3, SW3-1, SW3-2: switch
CS, CS1, CS2, CS2-1, CS2-2: control signal line
A: opening

What is claimed is:

1. An ultrasound probe comprising:
a transducer array consisting of a plurality of transducers that irradiate a subject with an ultrasonic wave and receive a reflected wave from the subject; and
a connection circuit for electrically connecting an apparatus main body of an ultrasound diagnostic apparatus and the transducer array,
wherein the transducer array includes a plurality of main transducers arranged in a major axis direction and consisting of
a plurality of center-side main transducers located on a center side of the arrangement,
a plurality of first end-side main transducers located on a first end side of the arrangement with respect to the plurality of center-side main transducers, and
a plurality of second end-side main transducers located on a second end side opposite to the first end side of the arrangement with respect to the plurality of center-side main transducers, and
the connection circuit includes
a first circuit connecting the apparatus main body and a center-side main transducer of the plurality of center-side main transducers, and
a second circuit having a plurality of main transducer switching switches for switching a connection destination of the apparatus main body between (i) a first end-side main transducer of the plurality of first end-side main transducers and (ii) a second end-side main transducer of the plurality of second end-side main transducers located on the second end side opposite to the first end side of the arrangement.

2. The ultrasound probe according to claim 1,
wherein each of the main transducer switching switches switches the connection destination of the apparatus main body between a k-th first end-side main transducer from the first end side among the plurality of first end-side main transducers in the arrangement and a k-th second end-side main transducer from a side of the plurality of center-side main transducers among the plurality of second end-side main transducers.

3. The ultrasound probe according to claim 1,
wherein the first circuit is provided on a first substrate, and
the second circuit is provided on a second substrate different from the first substrate.

4. The ultrasound probe according to claim 1,
wherein the transducer array includes a plurality of sub-transducers disposed on both sides of the plurality of respective main transducers in a minor axis direction orthogonal to the major axis direction, and
the first circuit and the second circuit each include a sub-transducer switching switch for switching between connection and non-connection between a signal line connected to (a) a main transducer of the plurality of main transducers and (b) the plurality of sub-transducers disposed on both sides of the main transducer in the minor axis direction.

5. An ultrasound diagnostic apparatus comprising:
the ultrasound probe according to claim 1;
a transmission and reception circuit that transmits a transmission signal to the ultrasound probe, and that performs signal processing on a reception signal from the ultrasound probe; and
a switch control circuit that controls switching of the main transducer switching switch, wherein in a state in which the apparatus main body and the first end-side main transducer are connected to each other, the transmission and reception circuit transmits the transmission signal to the first end-side main transducer and the plurality of center-side main transducers, and then moves an opening formed from plural main transducers of the plurality of main transducers which are targets of transmission of the transmission signal toward the second end side, the switch control circuit switches the main transducer switching switch so that the apparatus main body and the second end-side main transducer are connected to each other, when an end of the opening on the second end side has reached an end of the center-side main transducer on the second end side, and in a state in which the apparatus main body and the second end-side main transducer are connected to each other, the transmission and reception circuit transmits the transmission signal to the plurality of center-side main transducers and the second end-side main transducer, and then moves the opening toward the second end side.

6. The ultrasound diagnostic apparatus according to claim 5, wherein the plurality of first end-side main transducers are divided into a plurality of first end-side blocks, each of which is a unit for performing switching control of the main transducer switching switch, and each including plural first end-side main transducers which are successive in the arrangement, the plurality of second end-side main transducers are divided into a plurality of second end-side blocks, each of which is a unit of switching control of the main transducer switching switch, each corresponding respectively to each of the plurality of first end-side blocks according to the arrangement, and each including plural second end-side main transducers which are successive in the arrangement, in a state in which the apparatus main body and each first end-side block of the plurality of first end-side blocks are connected to each other, the transmission and reception circuit transmits the transmission signal to the first end-side block and a part of the plurality of center-side main transducers, and then moves an opening formed from plural main transducers of the plurality of main transducers which are targets of transmission of the trans mission signal toward the second end side, the switch control circuit switches the main transducer switching switch so that the apparatus main body is disconnected from a first end-side first block which is the first end-side block positioned at a position closest to the first end, and the apparatus main body and a second end-side first block which is the second end-side block adjacent to the center-side main transducer are connected to each other, when an end of the opening on the second end side has reached an end of the center-side main transducer on the second end side, and in a state in which the apparatus main body is connected to one or more of the plurality of first end-side blocks other than the first end-side first block and the second end-side first block, the transmission and reception circuit transmits the transmission signal to the one or more of the plurality of first end-side blocks other than the first end-side first block, the plurality of center-side main transducers, and the plural second end-side main transducers included in the second end-side first block, and then moves the opening toward the second end side.

7. The ultrasound diagnostic apparatus according to claim 6, wherein a maximum width APmax of the opening is represented by:

$$AP\text{max} = USch - N$$

wherein $USch = T - (B \times N)$, wherein T represents the number of the plurality of transducers, B represents the number of the first end-side blocks or the second end-side blocks, and N represents the number of transducers included in one first end-side block or one second end-side block.

* * * * *